United States Patent
Zablocki et al.

(10) Patent No.: US 7,300,923 B2
(45) Date of Patent: *Nov. 27, 2007

(54) PARTIAL AND FULL AGONISTS OF A1 ADENOSINE RECEPTORS

(75) Inventors: Jeff Zablocki, Mountain View, CA (US); Elfatih Elzein, Fremont, CA (US); Michael Organ, Burlington (CA); Yaroslav Bilokin, Toronto (CA); Stanislas Mayer, Eschau (FR); Anthony Disanti, Erie, PA (US); Scott Miller, Wilmington, DE (US); Peter Kernast, Hamilton, NJ (US)

(73) Assignee: CV Therapeutics, Inc., Palo Alto, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 11/214,706

(22) Filed: Aug. 29, 2005

(65) Prior Publication Data

US 2006/0052330 A1  Mar. 9, 2006

Related U.S. Application Data

(60) Provisional application No. 60/606,083, filed on Aug. 30, 2004, provisional application No. 60/622,076, filed on Oct. 26, 2004.

(51) Int. Cl.
- *A01N 43/04* (2006.01)
- *A61K 31/70* (2006.01)
- *C07H 19/16* (2006.01)
- *C07H 19/167* (2006.01)
- *C07H 19/173* (2006.01)
- *C07D 473/00* (2006.01)

(52) U.S. Cl. .................. 514/46; 514/263.1; 536/27.3; 536/27.6; 536/27.62; 544/264; 544/277

(58) Field of Classification Search .................. None
See application file for complete search history.

(56) References Cited

U.S. PATENT DOCUMENTS

| 5,587,392 | A  | * | 12/1996 | Murakami et al. | .......... 514/359 |
| 6,946,449 | B2 |   | 9/2005  | Elzein et al.   |                   |
| 7,005,424 | B2 | * | 2/2006  | Hung et al.     | .................. 514/44 |
| 2003/0216349 | A1 |   | 11/2003 | Belardinelli et al. | |
| 2004/0044225 | A1 | * | 3/2004  | Kanter et al.   | .................. 549/23 |
| 2005/0020532 | A1 |   | 1/2005  | Elzein et al.   | |
| 2006/0009417 | A1 | * | 1/2006  | Elzein et al.   | ................. 514/46 |

OTHER PUBLICATIONS

Jaworski, J. S. "Nonequilibrium Solvent Polarization in Kinetics of SN2 Reactions," International Journal of Chemical Kinetics, vol. 35, No. 2, 2003, pp. 61-66.*

Van Tilburg et al, "$N^6,5'$—Disubstituted Adenosine Derivatives as Partial Agonists for the Human Adenosine $A^3$ Receptor", J. Med. Chem., Division of Medicinal Chemistry, Leiden/Amsterdam Center for Drug Research, The Netherlands; 1999, vol. 42, pp. 1393-1400.

Robins M.J. et al., "Nucleic Acid Related Compounds. 66. Improved Syntheses of 5'-Chloro-5'-Thionucleosides", Canadian Journal of Chemistry, National Research Council, Ottawa, Canada, vol. 69, No. 9, 1991, pp. 1468-1474.

* cited by examiner

*Primary Examiner*—Shaojia Anna Jiang
*Assistant Examiner*—Layla Bland
(74) *Attorney, Agent, or Firm*—J. Elin Hartrum; Brian Lewis; CV Therapeutics, Inc.

(57) ABSTRACT

Disclosed are syntheses suitable for large scale manufacture of novel compounds that are partial and full $A_1$ adenosine receptor agonists, useful for treating various disease states, in particular tachycardia and atrial flutter, angina, and myocardial infarction.

25 Claims, No Drawings

PARTIAL AND FULL AGONISTS OF A1 ADENOSINE RECEPTORS

CROSS REFERENCE TO RELATED APPLICATIONS

This application claims priority to U.S. Provisional Patent Application Ser. No. 60/606,083, filed Aug. 30, 2004, and to U.S. Provisional Patent Application Ser. No. 60/622,076, filed Oct. 26, 2004, the complete disclosures of which are hereby incorporated by reference.

FIELD OF THE INVENTION

The present invention relates to the preparation of compounds that are partial or full $A_1$ adenosine receptor agonists. The compounds are useful for treating mammals with diabetic disorders, obesity, modifying adipocyte function, CNS disorders, and modifying cardiac activity, in particular treatment of arrhythmia. The compounds also have antilipolytic effects in mammals.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148-153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499-1509 and J. C. Shryock and L. Belardinelli The Am. J. Cardiology, Vol. 79 (1997) P 2-10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli Circulation, Vol. 83 (1991), P 1499-1509 and J. C. Shryock and L. Belardinelli, Am. J. Cardiology, Vol. 79 (1997) P 2-10.

$A_1$ agonists, as a result of their inhibitory action on cyclic AMP generation, have antilipolytic effects in adipocytes that lead to a decreased release of nonesterified fatty acids (NEFA) (E. A. van Schaick et al J. Pharmacokinetics and Biopharmaceutics, Vol. 25 (1997) p 673-694 and P. Strong Clinical Science Vol. 84 (1993) p. 663-669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128-1136 and G. Boden et al J. Clin. Invest. Vol. 93 (1994) p 2438-2446). The hypothesis of a glucose fatty acid cycle was proposed by P. J. Randle as early as 1963 (P. J. Randle et al Lancet (1963) p. 785-789). A tenet of this hypothesis would be that limiting the supply of fatty acids to the peripheral tissues should promote carbohydrate utilization (P. Strong et al Clinical Science Vol. 84 (1993) p. 663-669).

The benefit of an $A_1$ agonist in central nervous disorders has been reviewed (L. J. S. Knutsen and T. F. Murray in Purinergic Approaches in Experimental Therapeutics, Eds. K. A. Jacobson and M. F. Jarvis (1997) Wiley-Liss, N.Y., P-423-470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221-228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239-243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479-487). A second area where an $A_1$ adenosine agonist has a benefit is in animal models of forebrain ishemia as demonstrated by Knutsen et al (J. Med. Chem. Vol. 42 (1999) p. 3463-3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

A class of compounds that are potent $A_1$ adenosine receptor agonists, full and/or partial, has been reported (see U.S. patent application Ser. No. 10/194,335, filed Jul. 17, 2002, the complete disclosure of which is hereby incorporated by reference). One compound disclosed in this patent application, identified as (4S,5S,2R,3R)-5-[(2-fluorophenylthio) methyl]-2-{6-[(2-hydroxy-cyclopentyl)amino]-purin-9-yl}oxolane-3,4-diol, has been shown to be a highly selective partial $A_1$-adenosine receptor agonist.

Given the heightened interest in this and similar compounds, in particular the diastereoisomers of (4S,5S,2R,3R)-5-[(2-fluorophenylthio)methyl]-2-{6-[(2-hydroxy-cyclopentyl)amino]-purin-9-yl}oxolane-3,4-diol, it has become desirable to find a new method of synthesis that provides a convenient method for making large quantities of such compounds in good yield and high purity, avoiding the use of chromatography and other labor-intensive separation steps.

SUMMARY OF THE INVENTION

Thus, it is an object of this invention to provide a convenient synthesis for the large scale preparation of (4S,5S,2R,3R)-5-[(2-fluorophenylthio)methyl]-2-{6-[(2-hydroxy-cyclopentyl)amino]-purin-9-yl}oxolane-3,4-diol and related compounds, and its diastereoisomers, in particular 2-{6-[((1S,2S)-2-hydroxycyclopentyl)amino]purin-9-yl}(4S,5S,3R)-5-[(2-fluorophenylthio)methyl]oxolane-3,4-diol and 2-{6-[((1R,2R)-2-hydroxycyclopentyl)amino]purin-9-yl}(4S,5S,3R)-5-[(2-fluorophenylthio)methyl]-oxolane-3,4-diol. Accordingly, in a first aspect, the invention relates to the preparation of compounds of Formula I:

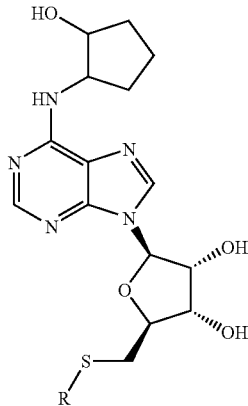

Formula I wherein R is optionally substituted phenyl:
comprising contacting a compound of the formula (5):

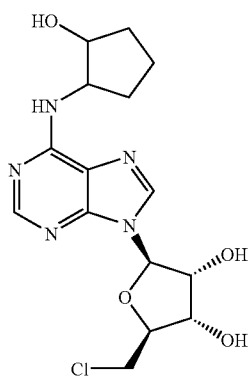

(5)

with a compound of the formula RSH in the presence of a base.

In a preferred embodiment R is 2-fluorophenyl and the 6-substituent is (1R,2R)-2-hydroxycyclopentyl)amino.

Examples of suitable bases are sodium hydroxide, sodium carbonate, potassium carbonate, triethylamine, preferably potassium carbonate, and the reaction is typically conducted in a polar solvent, for example N,N-dimethylformamide or N,N-dimethylacetamide.

In a second aspect, the invention relates to the preparation of the compound of formula (5), comprising contacting the compound of formula (13);

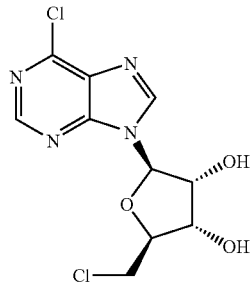

(13)

with 2-hydroxycyclopentylamine in the presence of a base to provide a compound of formula (5).

The reaction is typically conducted in a protic solvent, for example ethanol or isopropanol, or alternatively dichloromethane. Examples of suitable bases are sodium hydroxide, potassium carbonate, and triethylamine, preferably triethylamine. In a preferred embodiment, the 2-hydroxycyclopentylamine is present as a single isomer, namely (1R,2R)-2-hydroxycyclopentylamine.

In a third aspect, the invention relates to the preparation of the compound of formula (13), comprising contacting the compound of formula (12);

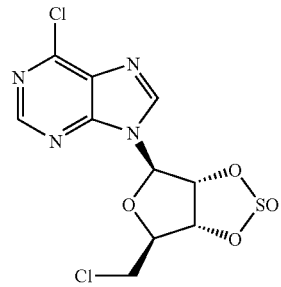

(12)

with a base.

The preferred base is aqueous ammonia, and the reaction is typically carried out in an inert solvent, for example methanol or dichloromethane.

In a fourth aspect, the invention relates to the preparation of a compound of formula (12), comprising contacting 6-chloropurine riboside, that is a compound of the formula (1):

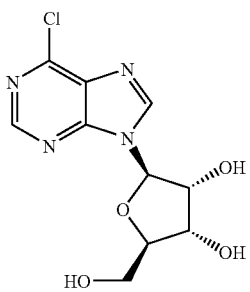

with thionyl chloride in the presence of a base;

In a preferred embodiment the reaction is conducted in the presence of an inert solvent, for example acetonitrile or dichloromethane. The base is typically pyridine.

In a fifth aspect, the invention relates to the preparation of compounds of Formula I:

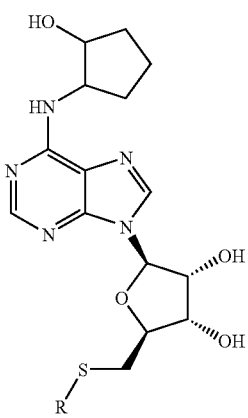

Formula I wherein R is optionally substituted phenyl:
comprising the steps of:
(a) contacting a compound of the formula (1):

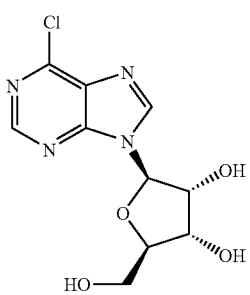

with thionyl chloride in the presence of a base;

(b) contacting the product of step (a) with a base to form a compound of formula (13):

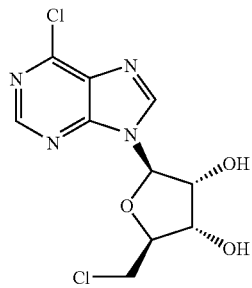

(c) contacting the product of step (b) with 2-hydroxycyclopentylamine in the presence of a base to provide a compound of formula (5);

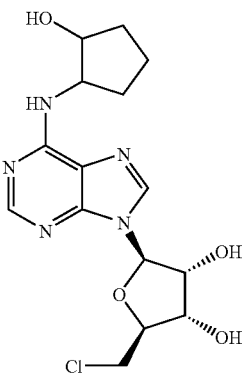

and;

(d) contacting the product of step (c) with a compound of the formula RSH in the presence of a base, in which R is as defined above.

Preferred Embodiments

In step (a), the reaction is typically conducted in the presence of an inert solvent, for example acetonitrile or dichloromethane. The base is typically pyridine.

In step (b), the base is typically aqueous ammonia. The reaction is preferably conducted in the presence of an inert solvent.

In step (c), the reaction is carried out in an inert solvent, the preferred base is triethylamine, and the 2-hydroxycyclopentylamine is preferably present as a single isomer, namely (1R,2R)-2-hydroxycyclopentylamine.

In step (d) the preferred solvent is N,N-dimethylformamide or N,N-dimethylacetamide, more preferably N,N-dimethylacetamide, and the preferred base is potassium carbonate.

It is preferred that the products of formula steps (a) and (b), the compounds of formula (12) and (13), are not isolated, but used as the crude product in the subsequent reaction step. In this manner, the process eliminates costly and time-consuming purification steps, which is a significant consideration when carrying out a large scale process.

DEFINITIONS AND GENERAL PARAMETERS

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain having from 1 to 6 carbon atoms.

The term "substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1-20 atoms as defined above.

Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxyethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo [2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

The compounds of Formula I include the definition that "R and YR$^1$ when taken together with the nitrogen atom to which they are attached represents optionally substituted heterocyclyl". Such a definition includes heterocycles with only nitrogen in the ring, for example pyrrolidines and piperidines, and also includes heterocycles that have more than one heteroatom in the ring, for example piperazines, morpholines, and the like.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

The term "protic solvent" in general refers to a solvent containing a hydroxy group. Examples pf protic solvents are methanol, ethanol, n-propanol, isopropanol, butanol, and the like.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethylamine, diethylamine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279-286), and less likely to cause side effects.

Nomenclature

The naming and numbering of the compounds of the invention is illustrated with a representative compound of Formula I in which R is 2-fluorophenyl:

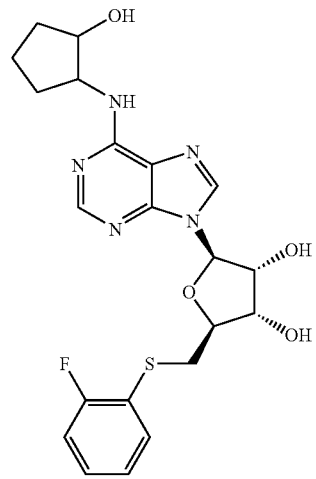

which is named:
(4S,5S,2R,3R)-5-[(2-fluorophenylthio)methyl]-2-{6-[(2-hydroxycyclopentyl)amino]-purin-9-yl}oxolane-3,4-diol, or:
2-{6-[((1RS,2RS)-2-hydroxycyclopentyl)amino]purin-9-yl}(4S,5S,3R)-5-[(2-fluorophenylthio)methyl]oxolane-3,4-diol.

The related compound in which the 6-amino substituent is derived from (1S,2S)-2-aminocyclopentan-1-ol is named 2-{6-[((1S,2S)-2-hydroxycyclopentyl)amino]purin-9-yl}(4S,5S,3R)-5-[(2-fluorophenylthio)methyl]oxolane-3,4-diol. The related compound in which the 6-amino substituent is derived from (1R,2R)-2-aminocyclopentan-1-ol is named 2-{6-[((1R,2R)-2-hydroxycyclopentyl)amino]purin-9-yl}(4S,5S,3R)-5-[(2-fluorophenylthio)methyl]-oxolane-3,4-diol. The related compound in which the 6-amino substituent is derived from (1R,2S)-2-aminocyclopentan-1-ol is named 2-{6-[((1R,2S)-2-hydroxycyclopentyl)amino]purin-9-yl}(4S,5S,3R)-5-[(2-fluorophenylthio)methyl]-oxolane-3,4-diol. The related compound in which the 6-amino substituent is derived from (1S,2R)-2-aminocyclopentan-1-ol is named 2-{6-[((1S,2R)-2-hydroxycyclopentyl)amino]purin-9-yl}(4S,5S,3R)-5-[(2-fluorophenylthio)methyl]-oxolane-3,4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide, ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

A process for the preparations of the compounds of Formula I, starting from 6-chloropurine riboside, is shown in Reaction Scheme I.

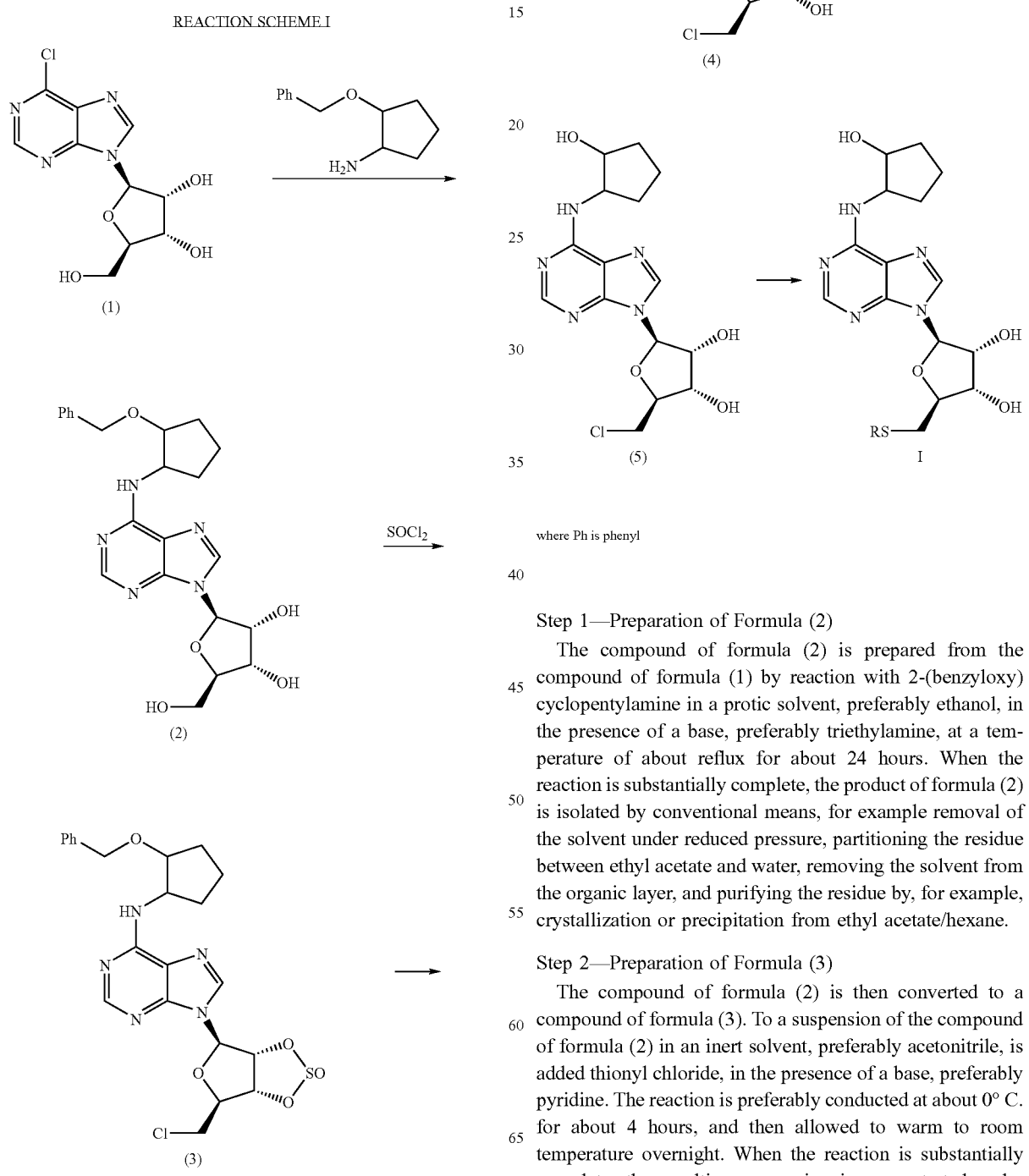

where Ph is phenyl

Step 1—Preparation of Formula (2)

The compound of formula (2) is prepared from the compound of formula (1) by reaction with 2-(benzyloxy) cyclopentylamine in a protic solvent, preferably ethanol, in the presence of a base, preferably triethylamine, at a temperature of about reflux for about 24 hours. When the reaction is substantially complete, the product of formula (2) is isolated by conventional means, for example removal of the solvent under reduced pressure, partitioning the residue between ethyl acetate and water, removing the solvent from the organic layer, and purifying the residue by, for example, crystallization or precipitation from ethyl acetate/hexane.

Step 2—Preparation of Formula (3)

The compound of formula (2) is then converted to a compound of formula (3). To a suspension of the compound of formula (2) in an inert solvent, preferably acetonitrile, is added thionyl chloride, in the presence of a base, preferably pyridine. The reaction is preferably conducted at about 0° C. for about 4 hours, and then allowed to warm to room temperature overnight. When the reaction is substantially complete, the resulting suspension is concentrated under reduced pressure to afford the compound of formula (3), which is taken to the next step without purification.

Step 3—Preparation of Formula (4)

The compound of formula (4) is prepared from the compound of formula (3) by dissolving (3) in a mixture of a base, preferably ammonium hydroxide, and a protic solvent, preferably methanol. The reaction is carried out at about room temperature, for about 30 minutes. When the reaction is substantially complete, the product of formula (4) is isolated by conventional means, for example by removal of the solvent under reduced pressure, partitioning the residue between ethyl acetate and water. and removing ethyl acetate under reduced pressure. The residue is used in the next step with no further purification.

Step 4—Preparation of Formula (5)

The compound of formula (4) is then deprotected by treatment with a partially unsaturated cycloalkyl compound, preferably cyclohexene, in the presence of a catalyst, preferably palladium hydroxide. Alternatively, ammonium formate can be used in place of cyclohexene. The reaction is conducted in a protic solvent, preferably ethanol, preferably at about reflux, for about 18 hours. When the reaction is substantially complete, the product of formula (5) is isolated by conventional means, for example by removal of the solvent under reduced pressure, followed by trituration of the residue.

Step 5—Preparation of Formula I

The compound of formula (5) is then reacted with a compound of formula RSH, preferably 2-fluorothiophenol. The reaction is conducted in a polar solvent, preferably N,N-dimethylformamide, in the presence of a base, for example sodium hydroxide, at a temperature of about 100° C. for about 3-5 hours. Alternatively, the reaction is conducted in a polar solvent, preferably N,N-dimethylformamide, in the presence of an tertiary base, preferably triethylamine, at about room temperature for about 1-5 days, preferably about 3 days. When the reaction is substantially complete, the product of Formula I is isolated by conventional means, for example by removal of the solvent under reduced pressure, and triturating the residue with diethyl ether.

Preparation of Starting Materials 1,2-(Benzyloxy)-cyclopentylamine is used as a starting material in step 1. This compound, as the racemic mixture or as the individual isomers, is either commercially available or can be made by methods well known to those skilled in the art. For example, one method of making (1R,2R)-2-(benzyloxy)-cyclopentylamine is shown in Reaction Scheme II below.

REACTION SCHEME II

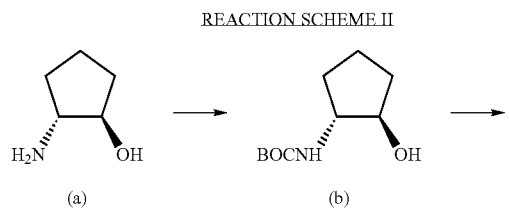

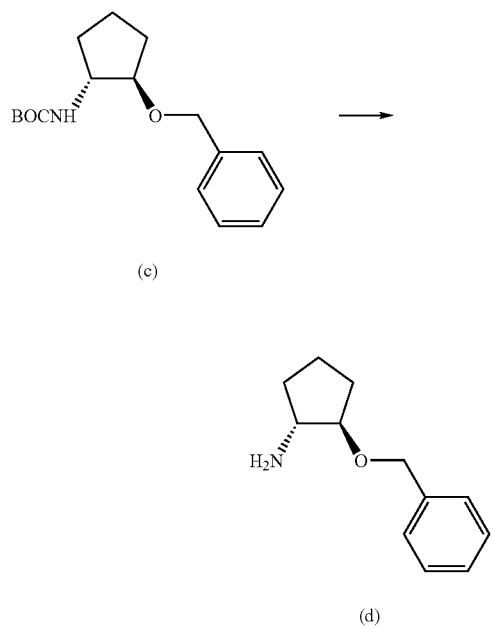

In the first step, the compound of formula (a) ((1R,2R)-2-aminocyclopentan-1-ol) is N-protected with (BOC)₂O (di-t-butyl dicarbonate) by conventional means, for example by reaction in an inert solvent in the presence of 4-dimethylaminopyridine. The protected cyclopentanol (b) derivative is then reacted with benzyl bromide in the presence of a base, preferably sodium hydride, to form (c), which is then deprotected in a conventional manner, with hydrochloric acid in dioxane, for example.

Starting with (1S,2S)-2-aminocyclopentan-1-ol provides a compound with the opposite stereochemistry to formula (d), and starting with (1RS,2RS)-2-aminocyclopentan-1-ol provides a racemic analog of the compound of formula (d).

An alternative process for the preparation of compounds of Formula I is shown in Reaction Scheme III.

REACTION SCHEME III

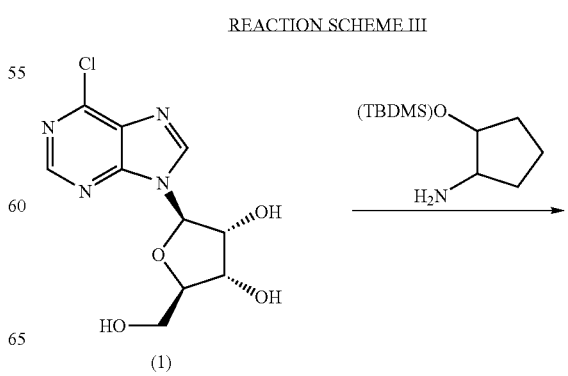

-continued

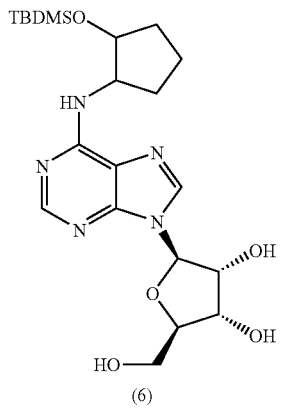
(6)

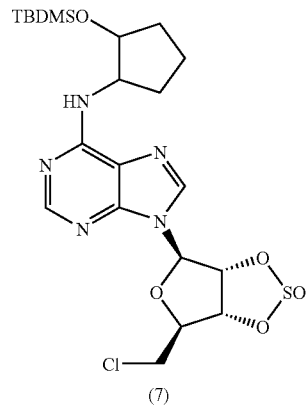
(7)

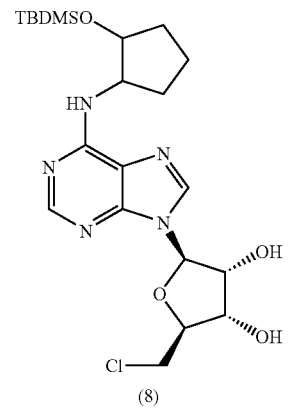
(8)

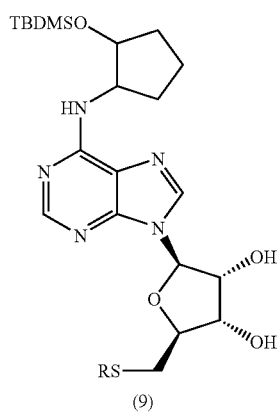
(9)

SOCl₂ →

→

→

-continued

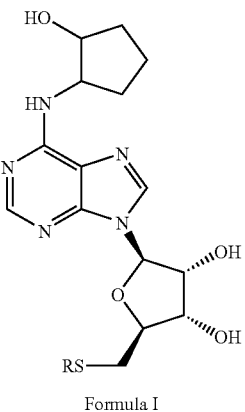
Formula I

The starting protected cyclopentyl derivative can be derived from (1R,2R)-2-aminocyclopentan-1-ol, (1S,2S)-2-aminocyclopentan-1-ol, or (1RS,2RS)-2-aminocyclopentan-1-ol. The hydroxy group is protected as a t-butyldimethylsilyl group by methods well known in the art.

Alternatively, the compounds of Formula I can be conveniently synthesized without using any protecting groups, as shown in Reaction Scheme IV.

REACTION SCHEME IV

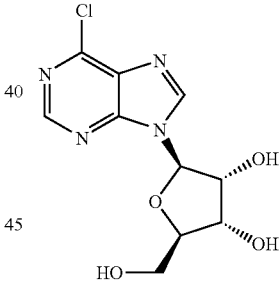
(1)

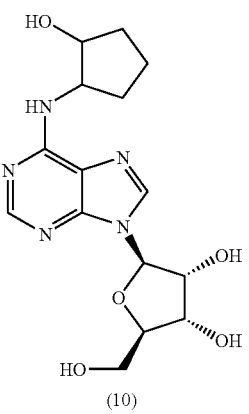
(10)

Tosyl chloride / LiCl →

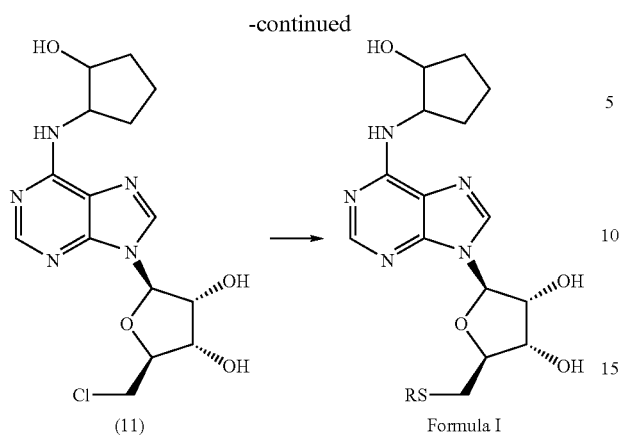

(11) → Formula I

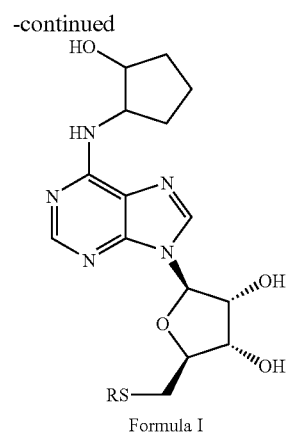

(5) → Formula I

A preferred method of preparing the compounds of Formula I without the necessity of using any protecting groups, or of isolating and/or purifying the intermediates, is shown in Reaction Scheme V.

REACTION SCHEME V

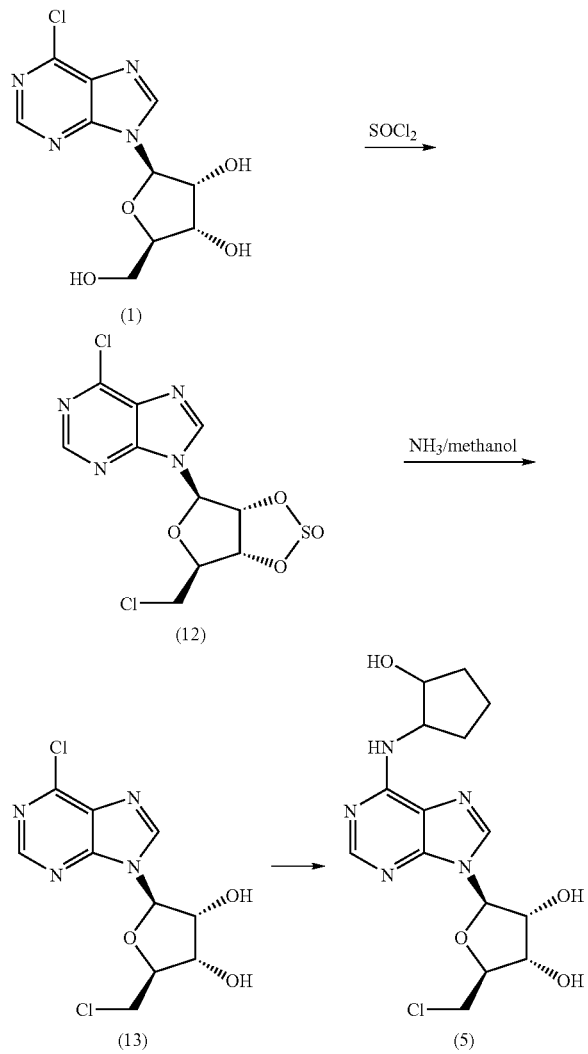

Step 1—Preparation of Formula (12)

The compound of formula (1) is converted to a compound of formula (12) by reaction with thionyl chloride. In general, the compound of formula (1) is suspended in an inert solvent, preferably acetonitrile, in the presence of about 2-2.5 molar equivalents of a base, preferably pyridine, and about 5-5.5 molar equivalents of thionyl chloride slowly added over a period of about 1 hour. The reaction is preferably conducted at about 0° C. for about 3 hours, and then allowed to warm to room temperature overnight. When the reaction is substantially complete, the resulting suspension is concentrated under reduced pressure to afford the compound of formula (12), which is preferably taken to the next step without purification.

Step 3—Preparation of Formula (13)

The compound of formula (13) is prepared from the compound of formula (12) by dissolving the crude product of step 1 in a mixture of a protic solvent, preferably aqueous methanol, and a base, preferably aqueous ammonia. The reaction is carried out at about 0° C. for about 1 hour followed by about 3 hours at room temperature. When the reaction is substantially complete, the product of formula (13) is isolated by conventional means, and used in the next step with no further purification.

Step 4—Preparation of Formula (5)

The compound of formula (5) is prepared from the crude product of step 3 (the compound of formula (13)) by reaction with about 1-1.1 molar equivalents of 2-hydroxycyclopentylamine in a protic solvent, preferably isopropanol, in the presence of about 3 molar equivalents of a base, preferably triethylamine, at a temperature of about reflux for about 24 hours. When the reaction is substantially complete, the product of formula (5) is isolated by conventional means, for example by removal of the solvent under reduced pressure and stirring the residue with water.

Step 5—Preparation of Formula I

The product of step 4 (the compound of formula (14)) is then reacted with about 3-5 molar equivalents of a compound of formula RSH, for example 2-fluorothiophenol. The reaction is conducted in a polar solvent, typically N,N-dimethylformamide, in the presence of about 5-6 molar equivalents of a base, for example sodium hydride, sodium hydroxide, or triethylamine, preferably triethylamine, at about room temperature for about 1-5 days, preferably about 3 days. When the reaction is substantially complete, the product of Formula I is isolated by conventional means. The product can be additionally purified by recrystallization from various solvents, for example methanol, ethanol, isopropanol or mixtures of methanol and ethanol. Alternatively, the product can be purified by recrystallization from or slurrying with ethyl acetate.

Utility, Testing and Administration

General Utility

The compounds of Formula I are effective in the treatment of conditions known to respond to administration of a partial or fill agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure, non-insulin-dependent diabetes mellitus, hyperglycemia, epilepsy (anticonvulsant activity), and neuroprotection. $A_1$ agonists also have antipolytic effects in adipocytes that leads to a decreased release of nonesterified fatty acids Testing Activity testing is conducted as described in those patents and literature citations referenced above, and in the Examples below, and by methods apparent to one skilled in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

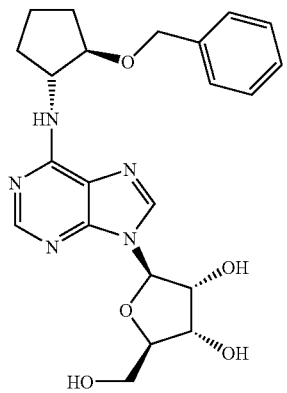

To a solution of 6-chloropurine riboside (10.0 g, 35 mmol) in ethanol (350 mL) was added triethylamine (10.0 mL, 100 mmol) and (1R,2R)-2-(benzyloxy)-cyclopentylamine (5.2 g, 52 mmol). The mixture was refluxed for 24 hours, during which the reaction went from a suspension to a clear solution. The ethanol was removed under reduced pressure, and the residue was partitioned between ethyl acetate and water (100 mL:200 mL). The organic layer was separated and the aqueous layer washed with ethyl acetate (2×75 mL). The combined organic layers were dried (sodium sulfate), and the solvent was removed under reduced pressure. The residue was dissolved in ethyl acetate (150 mL), and product precipitated by addition of hexane, to afford 2-(6-{[(1R,2R)-2-(phenylmethoxy)cyclopentyl]amino}purin-9-yl)(4S,3R, 5R)-5-(hydroxymethyl)oxolane-3,4-diol as a white solid, (12.0 grams, 77%).

$^1$H NMR (CD$_3$OD) δ 1.62-2.16 (m, 6 H), 3.26-3.29 (m, 1H, NHC<u>H</u>), 3.68-3.85 (m, 2H, CH$_2$-5'), 4.03-4.10 (m, 1H, CH-4'), 4.12-4.16 (m, 1H, CHOBn), 4.16-4.19 (m, 1H, 3'CH), 4.71 (s, 2H, OCH$_2$Ph), 4.83-4.92 (m, 1H, 2'CH), 5.98 (d, J=6 Hz, 1H, H-1'), 7.23-7.35 (m, 5H, PhH), 8.15 (S, 1H, C-2H).

B. Preparation of a Compound of Formula (2)

Similarly, following the procedure of 1A above, but replacing (1R,2R)-2-(benzyloxy)cyclopentylamine by other isomers of 2-(benzyloxy)cyclopentylamine, the following compounds are prepared:

2-(6-{[(1S,2S)-2-(phenylmethoxy)cyclopentyl]amino}purin-9-yl)(4S,3R,5R)-5-(hydroxymethyl)oxolane-3,4-diol;

2-(6-{[(1R,2S)-2-(phenylmethoxy)cyclopentyl]amino}purin-9-yl)(4S,3R,5R)-5-(hydroxymethyl)oxolane-3,4-diol;

2-(6-{[(1S,2R)-2-(phenylmethoxy)cyclopentyl]amino}purin-9-yl)(4S,3R,5R)-5-(hydroxymethyl)oxolane-3,4-diol; and 2-(6-{[(1RS,2RS)-2-(phenylmethoxy)cyclopentyl]amino}purin-9-yl)(4S,3R,5R)-5-(hydroxymethyl)oxolane-3,4-diol.

EXAMPLE 2

Preparation of a Compound of Formula (3)

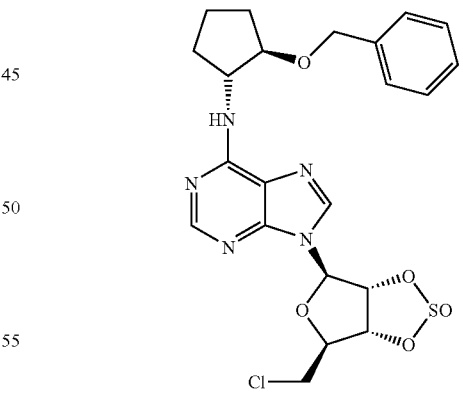

To a stirred suspension of 2-(6-{[(1R,2R)-2-(phenylmethoxy)cyclopentyl]-amino}purin-9-yl)(4S,3R,5R)-5-(hydroxymethyl)oxolane-3,4-diol (2.0 g, 4.5 mmol) in acetonitrile (15 mL) and pyridine (0.728 mL, 9 mmol) at 0 C was added dropwise thionyl chloride (1.7 mL, 22.5 mmol). After stirring for 4 hours at 0 C, the reaction was allowed to warm to room temperature, and then stirred overnight. Solvent was removed from the resulting suspension under reduced pressure, to afford 4-(6-{[(1R,2R)-2-(phenylmethoxy)cyclopentyl]amino}purin-9-yl)(6S,3aR,6aR)-6-(chloromethyl)-4H,
6H,3aH,6aH-oxolano[3,4-d]1,3,2-dioxathiolan-2-one,
which was taken to the next step without further purification.

B. Preparation of a Compound of Formula (3)

Similarly, following the procedure of 2A above, but replacing 2-(6-{[(1R,2R)-2-(phenylmethoxy)cyclopentyl]-amino}purin-9-yl)(4S,3R,5R)-5-(hydroxymethyl)oxolane-3,4-diol by other isomers of 2-(6-{[2-(phenylmethoxy)cyclopentyl]-amino}purin-9-yl)(4S,3R,5R)-5-(hydroxymethyl)oxolane-3,4-diol, the following compounds are prepared:

4-(6-{[(1S,2S)-2-(phenylmethoxy)cyclopentyl]
amino}purin-9-yl)(6S,3aR,6aR)-6-(chloromethyl)-4H,
6H,3aH,6aH-oxolano[3,4-d]1,3,2-dioxathiolan-2-one;

4-(6-{[(1R,2S)-2-(phenylmethoxy)cyclopentyl]
amino}purin-9-yl)(6S,3aR,6aR)-6-(chloromethyl)-4H,
6H,3aH,6aH-oxolano[3,4-d]1,3,2-dioxathiolan-2-one;

4-(6-{[(1S,2R)-2-(phenylmethoxy)cyclopentyl]
amino}purin-9-yl)(6S,3aR,6aR)-6-(chloromethyl)-4H,
6H,3aH,6aH-oxolano[3,4-d]1,3,2-dioxathiolan-2-one;
and 4-(6-{[(1RS,2RS)-2-(phenylmethoxy)cyclopentyl]
amino}purin-9-yl)(6S,3aR,6aR)-6-(chloromethyl)-4H,
6H,3aH,6aH-oxolano[3,4-d]1,3,2-dioxathiolan-2-one.

EXAMPLE 3

Preparation of a Compound of Formula (4)

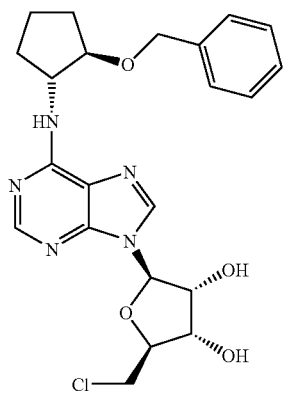

The 4-(6-{[(1R,2R)-2-(phenylmethoxy)cyclopentyl]amino}purin-9-yl)(6S,3aR,6aR)-6-(chloromethyl)-4H,6H,3aH,6aH-oxolano[3,4-d]1,3,2-dioxathiolan-2-one from Example 2 was dissolved in a mixture of methanol and water (40 mL/2 mL), and to this solution was added concentrated ammonium hydroxide (2.2 mL, 28%) dropwise. After stirring for 30 minutes at 23 C, the solvent was removed under reduced pressure and the residue diluted with water (15 mL). The aqueous mixture was extracted with ethyl acetate (3×75 mL), dried over MgSO4, and solvent removed under reduced pressure to provide 2-(6-{[(1R,2R)-2-(phenylmethoxy)cyclopentyl]amino}purin-9-yl)(4S,5S,3R)-5-(chloromethyl)oxolane-3,4-diol, which was used in the next step without further purification.

B. Preparation of a Compound of Formula (4)

Similarly, following the procedure of 3A above, but replacing 4-(6-{[(1R,2R)-2-(phenylmethoxy)cyclopentyl]amino}purin-9-yl)(6S,3aR,6aR)-6-(chloromethyl)-4H,6H,3aH,6aH-oxolano[3,4-d]1,3,2-dioxathiolan-2-one with other isomers of 4-(6-{[2-(phenylmethoxy)cyclopentyl]amino}purin-9-yl)(6S,3aR,6aR)-6-(chloromethyl)-4H,6H,3aH,6aH-oxolano[3,4-d]1,3,2-dioxathiolan-2-one, the following compounds are made:

2-(6-{[(1S,2S)-2-(phenylmethoxy)cyclopentyl]
amino}purin-9-yl)(4S,5S,3R)-5-(chloromethyl)oxolane-3,4-diol;

2-(6-{[(1R,2S)-2-(phenylmethoxy)cyclopentyl]
amino}purin-9-yl)(4S,5S,3R)-5-(chloromethyl)oxolane-3,4-diol;

2-(6-{[(1S,2R)-2-(phenylmethoxy)cyclopentyl]
amino}purin-9-yl)(4S,5S,3R)-5-(chloromethyl)oxolane-3,4-diol; and 2-(6-{[(1RS,2RS)-2-(phenylmethoxy)cyclopentyl]
amino}purin-9-yl)(4S,5S,3R)5-(chloromethyl)oxolane-3,4-diol.

EXAMPLE 4

Preparation of a Compound of Formula (5)

The 2-(6-{[(1R,2R)-2-(phenylmethoxy)cyclopentyl]amino}purin-9-yl)(4S,5S,3R)-5-(chloromethyl)oxolane-3,4-diol obtained in Example 3 (22 g) was dissolved in ethanol (450 mL) and cyclohexane (200 mL). To this solution was added palladium hydroxide (20 mole %, 1 gram added initially, 1 gram after 6 hours, and 1 gram after 14 hours), and the reaction mixture was refluxed for 18 hours. The reaction mixture was filtered thru celite while still hot, and solvent removed from the filtrate under reduced pressure. The product was triturated with ethanol (20 mL), filtered, and washed with ethanol, to afford 2-{6-[((1R,2R)-2-hydroxycyclopentyl)amino]purin-9-yl}(4S,5S,3R)-5-(chloromethyl)oxolane-3,4-diol as a white powder (7.3 grams).

Further material was recovered by suspending the retrieved palladium hydroxide in methanol (200 mL), and warming the mixture at 90° C. for 1 hour. The hot mixture was filtered thru celite, and the celite was further washed with hot methanol. The filtrate was concentrated under reduced pressure, and the residue triturated with ethanol (20 mL) to afford a further 8.6 grams of 2-{6-[((1R,2R)-2-hydroxycyclopentyl)amino]purin-9-yl}(4S,5S,3R)-5-(chloromethyl)oxolane-3,4-diol.

$^1$H NMR (DMSO-d6) δ 1.64-2.18 (m, 6 H), 3.26-3.29 (m, 1H, NHC$\underline{H}$), 3.83-3.97 (m, 2H, CH$_2$Cl 5'), 4.03-4.09 (m, 1H, CH-4'), 4.12-4.17 (m, 1H, CHOH), 4.16-4.19 (m, 1H, 3'CH), 4.84-4.92 (m, 1H, 2'CH), 5.96 (d, J=6 Hz, 1H, H-1'), 7.23-7.35 (m, 5H, PhH), 8.15 (S, 1H, C-2H), 8.39 (s, 1H, C-8H).

B. Preparation of a Compound of Formula (5)

Similarly, following the procedure of 4A above, but replacing 2-(6-{[(1R,2R)-2-(phenylmethoxy)cyclopentyl]amino}purin-9-yl)(4S,5S,3R)-5-(chloromethyl)oxolane-3,4-diol by other isomers of 2-(6-{[2-(phenylmethoxy)cyclopentyl]amino}purin-9-yl)(4S,5S,3R)-5-(chloromethyl)oxolane-3,4-diol, the following compounds are made:

2-(6-{[(1S,2S)-2-(phenylmethoxy)cyclopentyl]amino}purin-9-yl)(4S,5S,3R)-5-(chloromethyl)oxolane-3,4-diol;

2-(6-{[(1R,2S)-2-(phenylmethoxy)cyclopentyl]amino}purin-9-yl)(4S,5S,3R)-5-(chloromethyl)oxolane-3,4-diol;

2-(6-{[(1S,2R)-2-(phenylmethoxy)cyclopentyl]amino}purin-9-yl)(4S,5S,3R)-5-(chloromethyl)oxolane-3,4-diol; and 2-(6-{[(1RS,2RS)-2-(phenylmethoxy)cyclopentyl]amino}purin-9-yl)(4S,5S,3R)-5-(chloromethyl)oxolane-3,4-diol.

EXAMPLE 5

Preparation of a Compound of Formula I in which R is 2-Fluorophenyl

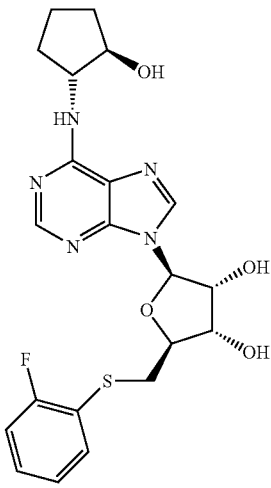

To a solution of 2-fluorothiophenol (38 mL, 406 mmol) in 2N sodium hydroxide (100 mL) was added 2-{6-[((1R,2R)-2-hydroxycyclopentyl)amino]purin-9-yl}(4S,5S,3R)-5-(chloromethyl)oxolane-3,4-diol (15.0 g, 40.6 mmol) in N,N-dimethylformamide (120 mL). The mixture was warmed to 100 C for 4 hours, following the progress of the reaction by TLC. The N,N-dimethylformamide was removed under reduced pressure, and the remaining mixture was diluted with water (200 mL), neutralized with acetic acid, extracted with ethyl acetate (3×125 mL), and the combined organic layers were dried over MgSO$_4$. After removing the solvent under reduced pressure the residue was triturated with diethyl ether and filtered, to afford 16 grams of 2-{6-[((1R,2R)-2-hydroxycyclopentyl)amino]purin-9-yl}(4S,5S,3R)-5-[(2-fluorophenylthio)methyl]oxolane-3,4-diol as a white powder (85% yield).

$^1$H NMR (DMSO-d6) δ 1.66-2.27 (m, 6 H), 3.42-3.59 (m, 1H, NHCH), 4.05-4.14 (m, 2H), 4.03-4.09 (m, 1H, CH-4'), 4.14-4.19 (m, 1H), 4.16-4.19 (m, 1H, 3'CH), 4.84-4.92 (m, 1H, 2'CH), 5.97 (d, J=6 Hz, 1H, H-1'), 7.05-7.55 (m, 4H, PhH), 8.10 (S, 1H, C-2H), 8.15 (s, 1H, C-8H).

B. Preparation of a Compound of Formula I in which R is 2-Fluorophenyl

Similarly, following the procedure of 5A above, but replacing 2-{6-[((1R,2R)-2-hydroxycyclopentyl)amino]purin-9-yl}(4S,5S,3R)-5-(chloromethyl)oxolane-3,4-diol by other isomers of 2-{6-[(2-hydroxycyclopentyl)amino]purin-9-yl}(4S,5S,3R)-5-(chloromethyl)oxolane-3,4-diol, the following compounds are made:

2-{6-[((1S,2S)-2-hydroxycyclopentyl)amino]purin-9-yl}(4S,5S,3R)-5-[(2-fluorophenylthio)methyl]oxolane-3,4-diol;

2-{6-[((1R,2S)-2-hydroxycyclopentyl)amino]purin-9-yl}(4S,5S,3R)-5-[(2-fluorophenylthio)methyl]oxolane-3,4-diol;

2-{6-[((1S,2R)-2-hydroxycyclopentyl)amino]purin-9-yl}(4S,5S,3R)-5-[(2-fluorophenylthio)methyl]oxolane-3,4-diol; and 2-{6-[((1RS,2RS)-2-hydroxycyclopentyl)amino]purin-9-yl}(4S,5S,3R)-5-[(2-fluorophenylthio)methyl]oxolane-3,4-diol.

C. Preparation of a Compound of Formula I Varying R

Similarly, following the procedure of 5A above, but replacing 2-fluorothiophenol by other thiophenols of formula RSH, other compounds of Formula I are prepared.

EXAMPLE 6

Preparation of a Compound of Formula (12)

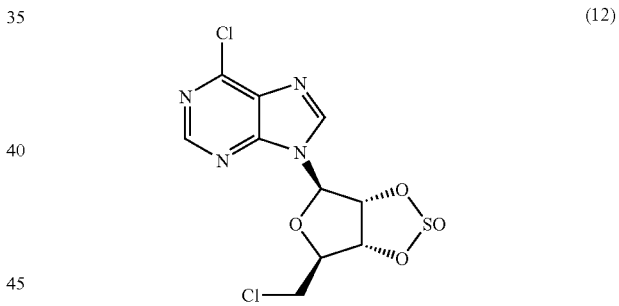

(12)

Preparation 1

To a cold (0° C., ice bath) suspension of 6-chloropurine riboside (50.0 g, 174.4 mmol) in dry acetonitrile (600 ml) and distilled pyridine (30 ml, 370 mmol) was added dropwise thionyl chloride (SOCl$_2$, 66.0 ml, 907 mmol) over a 55-minute period. The reaction mixture was stirred at 0° C. for 3 hours and then at room temperature for 18 hours. The yellow solution was concentrated at 40° C. under reduced pressure, and then dried under high vacuum for 6 hours. The residue, (6S,4R,3aR,6aR)-6-(chloromethyl)-4-(6-chloropurin-9-yl)-4H,6H,3aH,6aH-oxolano[3,4-d]1,3,2-dioxathiolan-2-one (12), was used in the next reaction with no further purification.

2. Alternative Preparation of a Compound of Formula (12)

To a mixture of 6-chloropurine riboside (1 Kg) in dry dichloromethane (15 liters) and distilled pyridine (850 ml) was added dropwise thionyl chloride (SOCl$_2$, 530 ml), maintaining the temperature at below 30° C. over period of 30-60 minutes. The reaction mixture was stirred at 30° C. for 4 hours, and then cooled to 20° C. Absolute ethanol (1700 ml) was added, maintaining the temperature at 20° C., and the mixture stirred for 15 minutes. Water (3.5 liters) was then added slowly, and the mixture stirred for 30 minutes, after which the contents were allowed to separate. The phases were separated, and the organic layer washed with saturated sodium bicarbonate 4 liters). After separation of the two phases, the organic layer was washed with saturated sodium chloride 2.6 liters), separated, and the solvent was removed under reduced pressure until a volume of approximately 4 liters was reached, providing a solution of (6S,4R,3aR,6aR)-6-(chloromethyl)-4-(6-chloropurin-9-yl)-4H,6H,3aH,6aH-oxolano[3,4-d]1,3,2-dioxathiolan-2-one (12) in solution, which was used in the next reaction with no further purification.

EXAMPLE 7

Preparation of a Compound of Formula (13)

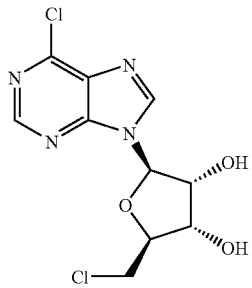

(13)

The compound of formula (12) obtained from Example 6 (preparation 1) was dissolved in methanol (1000 ml) and distilled water (50 ml). The solution was cooled to 0° C. and concentrated aqueous ammonia (28%, 56 ml) was added dropwise over 25 minutes. Stirring was continued at 0° C. for 1 hour and then at room temperature for 3 hours. During this time an additional 10 ml of concentrated aqueous ammonia (28%) was added (progress of the reaction was followed by TLC, $CH_2Cl_2$/MeOH, 9:1). The reaction mixture was then concentrated under reduced pressure and the residue was hydrolyzed with a 5% aqueous solution of citric acid (1000 ml) at room temperature. The aqueous layer was extracted with ethyl acetate (1×900 ml, 1×400 ml, 1×200 ml, 2×100 ml), and the combined organic layers were washed with saturated sodium bicarbonate (450 ml). The aqueous sodium bicarbonate layer was extracted with ethyl acetate (3×50 ml). The combined organic layers were washed with brine (400 ml), and the aqueous sodium chloride layer was also extracted with ethyl acetate (3×50 ml). The combined organic layers were dried over sodium sulfate, filtered, and the filtrate concentrated under reduced pressure to give 41.8 g of (4S,5S,2R,3R)-5-(chloromethyl)-2-(6-chloropurin-9-yl)oxolane-3,4-diol, the compound of formula (13). No further purification was carried out.

Preparation 2.

Alternatively, to the solution of 6S,4R,3aR,6aR)-6-(chloromethyl)-4-(6-chloropurin-9-yl)-4H,6H,3aH,6aH-oxolano[3,4-d]1,3,2-dioxathiolan-2-one (12) in solution obtained in Example 6, preparation 2, was added ammonium hydroxide (500 ml) and the mixture stirred at 25° C. for 12 hours. The solid was filtered off, and washed with dichloromethane (500 ml). The filtrate and the wash were combined, and the volume reduced under vacuum to about 6 liters. No further purification was carried out.

EXAMPLE 8

Preparation of a Compound of Formula (5)

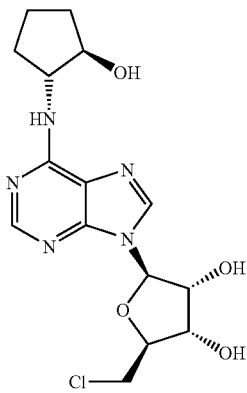

Preparation 1

To a suspension of (R,R)-2-aminopentanol hydrochloride (34.2 g, 249 mmol) in degassed isopropanol (100 ml) and distilled triethylamine (dried over calcium hydride, 95 ml, 69 g, 226 mmol) was added dropwise a solution of (4S,5S, 2R,3R)-5-(chloromethyl)-2-(6-chloropurin-9-yl)oxolane-3, 4-diol (36.3 g, 118.7 mmol) in 400 ml of isopropanol. The reaction mixture was stirred at room temperature for 30 minutes, and then refluxed (oil bath temperature: ~80° C.) for 20 hours. After cooling the reaction mixture to ambient temperature, the solvent was removed under reduced pressure, and 1000 ml of water was added to the residue. The suspension was stirred at room temperature for 3.5 hours, and the solid material filtered off, washed with water (1×60 ml and 1×90 ml), and dried under vacuum over $P_2O_5$ for 3 days to yield 68.0 g (81%) of 2-{6-[((1R,2R)-2-hydroxycyclopentyl)amino]purin-9-yl}(4S,5S,3R)-5-(chloromethyl) oxolane-3,4-diol as a light brown powder.

Preparation 2

Alternatively, the solution obtained in Example 7, preparation 2, was cooled to 20-25° C., and triethylamine (1000 ml) added, followed by (R,R)-2-aminopentanol (530 g). The mixture was refluxed for 8 hours, and then the solvent removed at atmospheric pressure until a volume of about 4 liters was reached. The mixture was cooled to 55-60° C., water (15 liters) added, and the mixture cooled to 20-25° C. The mix was stirred for about 1 hour, and then filtered, washing the solid with absolute ethanol (1.25 liters), and the solid dried under reduced pressure, not allowing the temperature to exceed 60° C.

B. Similarly, following the procedure of 8A (preparation 1 or preparation 2) above, but replacing (R,R)-2-aminopentanol hydrochloride with (S,S)-2-aminopentanol hydrochloride, 2-{6-[((1S,2S)-2-hydroxycyclopentyl)amino]purin-9-yl}(4S,5S,3R)-5-(chloromethyl)oxolane-3,4-diol is made.

C. Similarly, following the procedure of 8A (preparation 1 or preparation 2) above, but replacing (R,R)-2-aminopentanol hydrochloride with (1R,2S)-2-aminopentanol hydrochloride, 2-{6-[((1R,2S)-2-hydroxycyclopentyl)amino]purin-9-yl}(4S,5S,3R)-5-(chloromethyl)oxolane-3,4-diol is made.

D. Similarly, following the procedure of 8A (preparation 1 or preparation 2) above, but replacing (R,R)-2-aminopentanol hydrochloride with (1S,2R)-2-aminopentanol hydrochloride, 2-{6-[((1S,2R)-2-hydroxycyclopentyl)amino]purin-9-yl}(4S,5S,3R)-5-(chloromethyl)oxolane-3,4-diol is made.

EXAMPLE 9

Preparation of a Compound of Formula I in which R is 2-Fluorophenyl

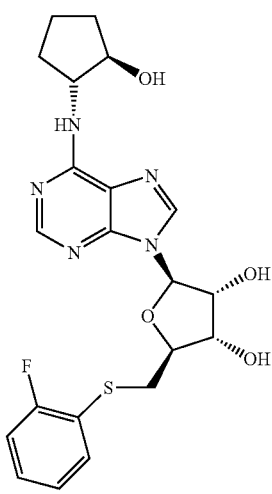

Preparation 1

To a solution of 2-{6-[((1R,2R)-2-hydroxycyclopentyl)amino]-purin-9-yl}(4S,5S,3R)-5-(chloromethyl)oxolane-3,4-diol (166.5 g, 0.457 mol) and triethylamine distilled from calcium hydride (352 ml, 256 g, 2.53 mol, 4 equivalents) in degassed anhydrous N,N-dimethylformamide (1.8 liters) was added 2-fluorothiophenol (190 ml, 228 g, 1.78 mol, 4 equiv) in 38 5 ml portions every 2-3 hours. The mixture was stirred at room temperature for 4 days with continuous bubbling of nitrogen into the solution (the reaction was monitored by $^1$H NMR). After the reaction was complete, the reaction mixture was poured into 7 liters of ethyl acetate, which was washed with 3 liters of water. The aqueous layer extracted with ethyl acetate (2×500 ml), and the combined organic layers were washed with water (3×2 liters), then reduced to a volume of about 1.8 liters, providing a suspension of a white solid. The suspension was stirred for 9 hours at room temperature, and the white precipitate filtered off, washed with diethyl ether (3×200 ml), and dried for 24 hours under high vacuum to give 131 g (63% yield) of 2-{6-[((1R,2R)-2-hydroxycyclopentyl)amino]purin-9-yl}(4S,5S,3R)-5-[(2-fluorophenylthio)methyl]-oxolane-3,4-diol as a white powder (98.9% pure).

$^1$H NMR (DMSO-d6) δ 1.66-2.27 (m, 6H), 3.42-3.59 (m, 1H, NHCH), 4.05-4.14 (m, 2H), 4.03-4.09 (m, 1H, CH-4'), 4.14-4.19 (m, 1H), 4.16-4.19 (m, 1H, 3'CH), 4.84-4.92 (m, 1H, 2'CH), 5.97 (d, J=6 Hz, 1H, H-1'), 7.05-7.55 (m, 4H, PhH), 8.10 (S, 1H, C-2H), 8.15 (s, 1H, C-8H).

The product was further purified by stirring in 1 liter of ethyl ether/ethanol (50:1) overnight, to give 127 g of pure 2-{6-[((1R,2R)-2-hydroxycyclopentyl)amino]purin-9-yl}(4S,5S,3R)-5-[(2-fluorophenylthio)methyl]-oxolane-3,4-diol.

Preparation 2

The product of Example 8, preparation 2 (1 Kg), was dissolved in N,N-dimethylacetamide (2.7 liters), and potassium carbonate (560 g) added. To the mixture, maintained at below 25° C., was added 2-fluorothiophenol (380 g), and the mixture was heated at 60-65 for about 6 hours. The mixture was then cooled to 25-30° C., and ethyl acetate (10 liters) added, followed by a solution of sodium chloride (260 g) in water (4.9 liters), and the mixture stirred for 15 minutes. After separation of the two layers, the organic phase was again washed with a solution of sodium chloride (260 g) in water (4.9 liters), and the mixture stirred for 15 minutes. After separation, the organic layer was concentrated at atmospheric pressure to a volume of about 5 liters, and methanol (10 liters) was added. The mixture was again concentrated at atmospheric pressure to a volume of about 2.8 liters, and the resulting solution cooled to about 35-40° C. Dichloromethane (5 liters) was then added, and the mixture maintained at about 35-40° C. for 1 hour, followed by cooling to between 0-5° C. for 30 minutes. The solid product was filtered off, washed with dichloromethane (2.8 liters), and dried under reduced pressure to constant weight, not allowing the temperature to rise above 50° C., to provide 2-{6-[((1R,2R)-2-hydroxycyclopentyl)amino]purin-9-yl}(4S,5S,3R)-5-[(2-fluorophenylthio)methyl]-oxolane-3,4-diol.

The product was further purified by dissolving 1 Kg of the product (2-{6-[((1R,2R)-2-hydroxycyclopentyl)amino]purin-9-yl}(4S,5S,3R)-5-[(2-fluorophenylthio)methyl]-oxolane-3,4-diol) in methanol (20 liters) at a temperature between 60-70° C., maintaining that temperature for 1 hour, cooling to 45-50° C., and then filtering the solution through a 1 micron filter, maintaining the solution temperature above 40° C. The solution was concentrated to about 7 liters, maintaining the solution temperature above 40° C., and the resultant solution was maintained at 50-55° C. for 1 hour. The solution was then cooled to −5° C. over a period of 2 hours, and the temperature maintained at −5° C. for 1 hour. The product was filtered off at −5° C., and the filtrate was used to wash the solid, to provide pure (2-{6-[((1R,2R)-2-hydroxycyclopentyl)amino]purin-9-yl}(4S,5S,3R)-5-[(2-fluorophenylthio)methyl]-oxolane-3,4-diol).

B. Preparation of a Compound of Formula I in which R is 2-Fluorophenyl

Similarly, following the procedure of 9A above (preparation 1 or 2), but replacing 2-{6-[((1R,2R)-2-hydroxycyclopentyl)amino]purin-9-yl}(4S,5S,3R)-5-(chloromethyl)oxolane-3,4-diol by other isomers of 2-{6-[(2-hydroxycyclopentyl)amino]purin-9-yl}(4S,5S,3R)-5-(chloromethyl)oxolane-3,4-diol, the following compounds are made:

2-{6-[((1S,2S)-2-hydroxycyclopentyl)amino]purin-9-yl}(4S,5S,3R)-5-[(2-fluorophenylthio)methyl]oxolane-3,4-diol;

2-{6-[((1R,2S)-2-hydroxycyclopentyl)amino]purin-9-yl}(4S,5S,3R)-5-[(2-fluorophenylthio)methyl]oxolane-3,4-diol;

2-{6-[((1S,2R)-2-hydroxycyclopentyl)amino]purin-9-yl}(4S,5S,3R)-5-[(2-fluorophenylthio)methyl]oxolane-3,4-diol; and 2-{6-[((1RS,2RS)-2-hydroxycyclopentyl)amino]purin-9-yl}(4S,5S,3R)-5-[(2-fluorophenylthio)methyl]oxolane-3,4-diol.

C. Preparation of a Compound of Formula I Varying R

Similarly, following the procedure of 9A (preparation 1 or 2) above, but replacing 2-fluorothiophenol by other thiophenols of formula RSH, other compounds of Formula I are prepared.

EXAMPLE 10

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 µg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer (5× volume of tissue mass pH=7.4). After centrifugation at 19,000 rpm for 25 minutes at 4° C., the supernatant was discarded, and the process was repeated twice. Compounds of Formula I were assayed to determine their affinity for the $A_1$ receptor in a pig striatum membrane prep or a $DDT_1$ membrane prep. Briefly, 0.2 mg of pig striatal membranes or $DDT_1$ cell membranes were treated with adenosine deaminase and 50 mM Tris buffer (pH=7.4) followed by mixing. To the pig membranes was added 2 µL of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for $DDT_1$ membranes in Tris buffer (50 mM, pH of 7.4) was added to achieve a final concentration of 2 nM. After incubation at 23 C for 2 h, then the solutions were filtered using a membrane harvester using multiple washing of the membranes (3×). The filter disks were counted in scintillation cocktail affording the amount of displacement of tritiated CPX or by the competitive binding of compounds of Formula I.

The compounds of Formula I are shown to be of high, medium, or low affinity for the $A_1$ adenosine receptor in this assay.

EXAMPLE 11

[$^{35}$S]GTPγS Binding Assays $A_1$-agonist stimulated [$^{35}$S] GTPγS binding was determined by a modification of the method described by Gierschkik et al. (1991) and Lorenzen et al. (1993). Membrane protein (30-50 µg) was incubated in a volume of 0.1 ml containing 50 mM Tris-HCl buffer pH 7.4, 5 mM $MgCl_2$, 100 mM NaCl, 1 mM dithiothreitol, 0.2 units ml$^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 µM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 µM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5-1000 nM GTPγS. At the end of the incubation, each suspension was filtered and the retained radioactivity determined as described above.

The compounds of Formula I are shown to be partial or full agonists of the $A_1$ adenosine receptor in this assay.

EXAMPLE 12 cAMP Assay

A scintillation proximity assay (SPA) using rabbit antibodies directed at cAMP using an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 µl of HBSS at 37° C. (5% $CO_2$ and 95% humidity). The partial or full $A_1$ agonists (5 µl) of this invention were incubated at various concentrations with the $DDT_1$ cells in the presence of rolipram (50 µM), and 5 µM forskolin for 10 min at 37° C. The cells were immediately lysed by treatment 5 µl of 10% dodecyltrimethylammonium bromide followed by shaking using microplate shaker. After incubation of the plate for 5 minutes, an immunoreagent solution (150 µl containing equal volumes of tracer, antiserum, and SPA fluorospheres) was added to each well followed by sealing the plate. After 15-20 h at 23° C., the amount of bound [$^{125}$I] cAMP to the fluoromicrospheres was determined by counting in a microtitre plate scintillation counter for 2 minutes. Comparison of counts with standard curves generated for cAMP using a similar protocol afforded the cAMP present after cell lysis.

The compounds of Formula I are shown to be functionally active as $A_1$ agonists with a partial or full decrease in cAMP in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, compostition of matter, process, process step or steps, to the objective, spirit and scope of the invention. All such modifications are intended to be within the scope of the claims appended hereto. All patents and publications cited above are hereby incorporated by reference.

What is claimed is:

1. A process for the preparation of a compound of Formula I:

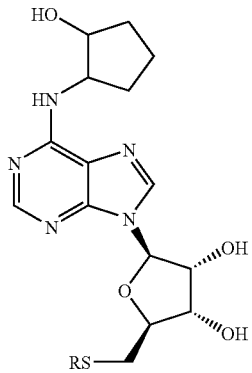

Formula I in which R is optionally substituted phenyl;
comprising:
contacting a compound of the formula:

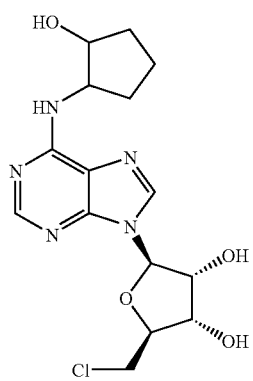

(5)

with a compound of the formula RSH in the presence of potassium carbonate in an inert solvent.

2. The process of claim 1, wherein R is 2-fluorophenyl, the 6-substituent is 6-((1R,2R)-2-hydroxycyclopentylamino), and the solvent is N,N-dimethylacetamide.

3. A process for the preparation of a compound of formula:

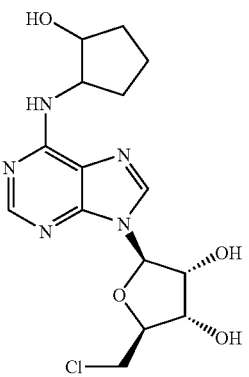

(5)

comprising;
contacting a compound of the formula:

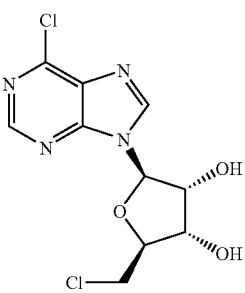

(13)

with a compound of the formula:

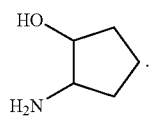

.

4. The process of claim 3, wherein the reaction is carried out in the presence of a base in an inert solvent.

5. The process of claim 4, wherein the base is chosen from sodium hydroxide or triethylamine.

6. The process of claim 5, wherein the base is triethylamine and the solvent is isopropanol or dichioromethane.

7. The process of claim 6, wherein R is 2-fluorophenyl and the 6-substituent is 6-((1 R,2R)-2-hydroxycyclopentylamino).

8. A process for the preparation of a compound of the formula:

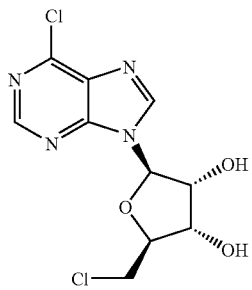

(13)

comprising:
contacting a compound of the formula:

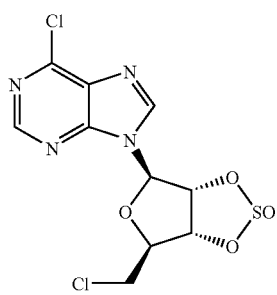

(12)

with a base.

9. The process of claim 8, wherein the base is ammonia.

10. The process of claim 9, wherein the reaction is conducted in methanol or dichloromethane.

11. A process for the preparation of the formula:

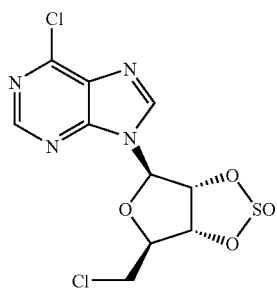

(12)

comprising:
contacting a compound of the formula:

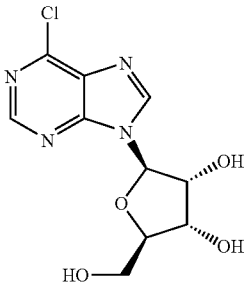

(1)

with thionyl chloride in the presence of a base.

12. The process of claim 11, wherein the base is pyridine.

13. The process of claim 12, wherein the reaction is conducted in dichloromethane.

14. A process for the preparation of a compound of Formula I:

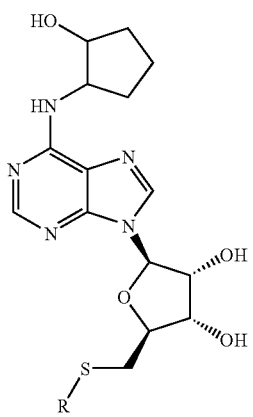

Formula I wherein R is optionally substituted phenyl:
comprising the steps of:
(a) contacting a compound of the formula (1):

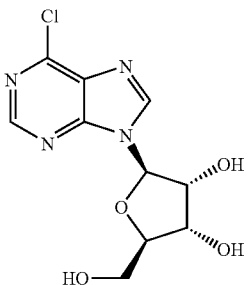

(1)

with thionyl chloride in the presence of a base;
(b) contacting the product of step (a) with a base to form a compound of formula (13):

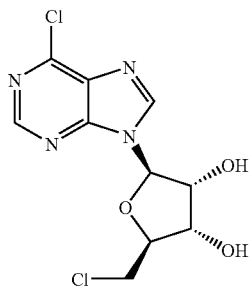

(13)

(c) contacting the product of step (b) with 2-hydroxycyclopentylamine in the presence of a base to provide a compound of formula (5);

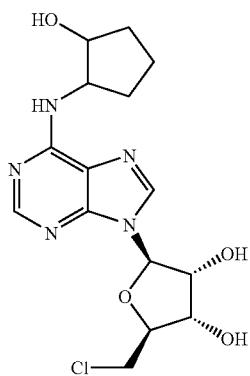

(5)

and;

(d) contacting the product of step (c) with a compound of the formula RSH in the presence of a base, in which R is as defined above.

15. The process of claim 14, wherein in step (a) the reaction is carried out in the presence of an inert solvent and a base.

16. The process of claim 15, wherein the inert solvent is dichloromethane and the base is triethylamine.

17. The process of claim 14, wherein in step (b) the base is aqueous ammonia.

18. The process of claim 17, wherein the reaction is conducted in methanol or dichloromethane.

19. The process of claim 14, wherein in step (c) the reaction is carried out in the presence of triethylamine in an inert solvent.

20. The process of claim 19, wherein the inert solvent is isopropanol or dichloromethane.

21. The process of claim 19, wherein R is 2-fluorophenyl and the 6-substituent is 6-((1R,2R)-2-hydroxycyclopentylamino).

22. The process of claim 14, wherein in step (d) the reaction is carried out in a solvent chosen from N,N-dimethylformamide and N,N-dimethylacetamide.

23. The process of claim 22, wherein the base is potassium carbonate.

24. The process of claim 22, wherein the solvent is N,N-dimethylacetamide.

25. The process of claim 22, wherein R is 2-fluorophenyl and the 6-substituent is 6-((1R,2R)-2-hydroxycyclopentylamino).

* * * * *